United States Patent [19]

Bender et al.

[11] Patent Number: 4,780,470
[45] Date of Patent: Oct. 25, 1988

[54] INHIBITION OF INTERLEUKIN-1 BY MONOCYTES AND/OR MACROPHAGES

[75] Inventors: Paul E. Bender, Cherry Hill, N.J.; Don E. Griswold, North Wales, Pa.; Nabil Hanna, Berwyn, Pa.; John C. Lee, Radnor, Pa.

[73] Assignee: SmithKline Beckman Corporation, Philadelphia, Pa.

[21] Appl. No.: 897,901

[22] Filed: Aug. 19, 1986

[51] Int. Cl.$^4$ ............................................. A61K 31/44
[52] U.S. Cl. .................................... 514/341; 514/825; 514/885
[58] Field of Search ................ 530/395; 514/825, 885, 514/396, 341; 548/335, 336

[56] References Cited

U.S. PATENT DOCUMENTS

| | | |
|---|---|---|
| 3,772,441 | 11/1973 | Lombardino et al. . |
| 3,929,807 | 2/1976 | Fitzi et al. . |
| 3,940,486 | 2/1976 | Fitzi et al. . |
| 4,159,338 | 6/1979 | Cherkofsky et al. . |
| 4,175,127 | 11/1979 | Bender et al. . |
| 4,182,769 | 1/1980 | Cherkofsky et al. . |
| 4,190,666 | 2/1980 | Cherkofsky et al. . |
| 4,199,592 | 4/1980 | Cherkofsky et al. . |
| 4,308,277 | 12/1981 | Ferrini et al. . |
| 4,461,770 | 7/1984 | Ferrini et al. . |

FOREIGN PATENT DOCUMENTS 845074 11/1977 Belgium .

OTHER PUBLICATIONS

Lombardino et al., *J. Med. Chem.*, 17 (11), 1182-1188 (1974).
Bender et al., *J. Med.*, 28, 1169-1177, (1985).
Zauer et al., *Chem Ber*, 106, 1628 (1973).
Tanino et al., *Bulletin of the Chemical Society of Japan*, 45, 1474-1480 (1972).
White et al., *J. Org. Chem.*, 29, 1926-1930 (1964).
Lantos et al., *J. Med. Chem.*, 27(1), 72-75 (1984).

*Primary Examiner*—Stanley J. Friedman
*Attorney, Agent, or Firm*—Carol G. Canter; Edward T. Lentz; Alan D. Lourie

[57] ABSTRACT

A method of inhibiting the production of interleukin-1 by monocytes in a human in need thereof which comprises administering to such human an effective interleukin-1 production inhibiting amount of a 4,5-diaryl-2(substituted)imidazole.

12 Claims, No Drawings

INHIBITION OF INTERLEUKIN-1 BY MONOCYTES AND/OR MACROPHAGES

BACKGROUND OF THE INVENTION

This invention relates to a method of inhibiting the production of interleukin-1 by monocytes and/or macrophages in a human in need thereof which comprises administering an effective, interleukin-1 production inhibiting amount of a 4,5-diaryl-2(substituted-)imidazole or a pharmaceutically acceptable salt thereof to such human.

Lombardino, et al., U.S. Pat. No. 3,772,441, issued Nov. 13, 1973, disclose compounds of the formula

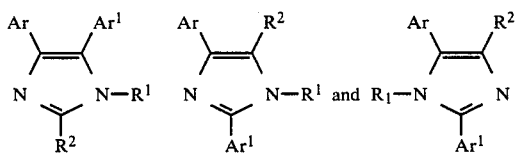

and the pharmaceutically acceptable acid addition salts thereof, wherein:

Ar and $Ar^1$ are each selected from furyl, thienyl, pyridyl, phenyl and substituted phenyl, wherein said substituents are selected from fluoro, chloro, bromo, and $C_{1-4}$ alkoxy;

$R^1$ is selected from H or $C_{1-4}$ alkyl; and $R^2$ is selected from trifluoromethyl, $C_{1-4}$ alkyl, furyl, thienyl, pyridyl, and substituted phenyl wherein said substituents are selected from fluoro, chloro, bromo, or $C_{1-4}$ alkoxy. Lombardino, et al. disclose that such compounds are antiinflammatory agents based on their activity in the carrageenan rat foot edema test. Such test is useful for detecting compounds which are cyclooxygenase inhibitors, but is of no known utility in detecting or suggesting compounds which are inhibitors of IL-1 production by macrophages and/or monocytes. Lombardino, et al. also state that such compounds are useful as antiarthritic agents but there is no further statement as to how such antiarthritic activity was determined. Such a blanket statement of antiarthritic activity does not disclose that such compounds are inhibitors of IL-1 production by macrophages and/or monocytes.

Lombardino, et al., J. Med. Chem., 17(11), 1182–1188 (1974) disclose compounds of the formula

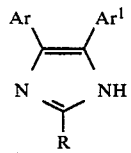

wherein Ar and $Ar^1$ are selected from methoxyphenyl, 4-ethoxyphenyl, 2-pyridyl and 4-halophenyl; and R is selected from 4-halophenyl, $CF_3$, phenyl and 4-methoxyphenyl. Lombardino, et al. disclose that some of such compounds have antiinflammatory activity in the carrageenan rat paw edema test which is useful for detecting compounds which are inhibitors of cyclooxygenase but is of no known utility of detecting or suggesting compounds which are inhibitors of IL-1 production by macrophages and/or monocytes.

Bender, et al., J. Med. Chem., 28. 1169–1177 (1985), disclose compounds of the formula

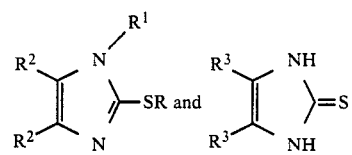

wherein R is methyl or ethyl, $R^1$ is H, methyl or ethyl, $R^2$ is 4-methoxyphenyl, and $R^3$ is 4-methyoxyphenyl, 4-bromophenyl or 3-fluorophenyl. Bender et al. also disclose that some of such compounds have antiarthritic activity in the rat adjuvant-induced arthritis assay and immunoregulatory activity in the mouse subliminal oxazolone-induced contact sensitivity assay. The adjuvant-induced arthritis assay is useful for detecting compounds which are cyclooxygenase inhibitors, but is of no known utility for detecting or suggesting compounds which are inhibitors of IL-1 production by macrophages and/or monocytes. The mouse subliminal oxazolone induced arthritis assay is useful for detecting compounds which are immunostimulants, but is of no known utility for detecting or suggesting compounds which are inhibitors of IL-1 production by macrophages and/or monocytes.

Cherkofsky, et al., U.S. Pat. No. 4,190,666, issued Feb. 26, 1980 disclose compounds of the formula

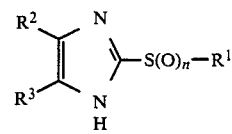

wherein:

n is 0, 1 or 2;

$R_1$ is $C_{1-6}$ alkyl or polyhalo $C_{1-6}$ alkyl; and $R_2$ and $R_3$ are independently selected from monosubstituted phenyl wherein said substituent is selected from $C_{1-4}$ alkoxy, chloro or fluoro. Cherkofsky, et al. also disclose that such compounds have antiinflammatory activity as determined by the established adjuvant-induced arthritis assay in rats, immunoregulatory effects as determined by the non-established adjuvant-induced arthritis assay in rats, and analgesic activity as determined by the phenylquinone writhing test. As stated above, the established adjuvant-induced arthritis test is of no known utility in detecting or suggesting compounds which are inhibitors of IL-1 production by macrophages and/or monocytes. The non-established adjuvant arthritis assay is useful for detecting compounds with cyclooxygenase inhibiting activity but is of no known utility for detecting or suggesting compounds which are inhibitors of IL-1 production by macrophages and/or monocytes. The phenylquinone writhing test is useful for detecting compounds with cyclooxygenase inhibiting activity but is of no known utility for detecting or suggesting compounds which are inhibitors of IL-1 production by macrophages and/or monocytes.

Zauer, et al., Chem Ber, 106, 1628–1636 (1973), disclose 4,5-bis(P-chlorophenyl)-2-(methylthio)imidazole and 4,5-bis(p-methoxyphenyl)-2-methylimidazole.

There is no disclosure in Zauer, et al. regarding any biological activity of such compounds.

Ferrini, et al., U.S. Pat. No. 4,308,277, issued Dec. 29, 1981, disclose compounds of the formula

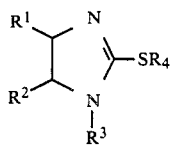

wherein:

$R_1$ and $R_2$ are independently selected from thienyl or monosubstituted phenyl, wherein said substituent is selected from lower alkoxy and halo;

$R^3$ is H or lower alkyl; and $R^4$ is lower alkyl.

Ferrini, et al. state that such compounds have immunoregulatory, antiinflammatory, antithrombolic and/or antinociceptive activity as exhibited by their activity in the Kaolin paw oedema assay in normal rats and adjuvantinduced arthritic assay in rats, the phenyl-p-benzoq inoneinduced writhing assay in mice, the iv administered acetic acid induced writhing assay in rats, the pulmonary embolism assay in rabbits, and an assay of inhibition of prostaglandin synthesis from arachidonic acid by spermatocystic enzymes in cattle. The kaolin paw oedema assay is useful for detecting compounds which are cyclooxygenase inhibitors, but is of no known utility in detecting compounds which are inhibitors of IL-1 production by macrophages and/or monocytes. As stated above, the phenyl-p-benzoquinone and adjuvant-induced arthritis assays are of no known utility in detecting or suggesting compounds which are inhibitors of IL-1 production by macrophages and/or monocytes. The iv-administered acetic acid induced writhing assay in rats is useful for detecting compounds which are cyclooxygenase inhibitors. The assay of inhibition of prostaglandin synthesis induced by spermatocystic enzymes is useful for detecting compounds which are inhibitors of the cyclooxygenase pathway. None of the acetic acid induced writhing assay, pulmonary embolism assay or the prostaglandin synthesis assay of any known utility are useful for detecting or suggesting compounds which are inhibitors of IL-1 production by macrophages and/or monocytes.

Dupont, Belgian patent application No. 845,074, published November 2, 1977, disclose compounds of the formula

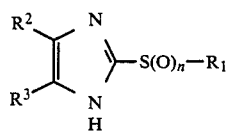

wherein:

n is 0, 1 or 2;

$R_1$ is mono or polyhalo $C_{1-4}$ alkyl or $C_{1-4}$ alkyl; and $R_2$ and $R_3$ are independently selected from monosubstituted phenyl wherein said substituent is selected from $C_{1-4}$ alkoxy, chloro or fluoro. Dupont discloses that such compounds have antiinflammatory and immunoregulatory properties based on their activity in the non-established and established adjuvant-induced arthritis assays in rats, both of which, as stated above, have no known utility in detecting or suggesting compounds which are inhibitors of IL-1 production by macrophages and/or monocytes.

Janino, et al., *Bulletin of the Chemical Society of Japan*, 45, 1474–1480 (1972), and White et al., *J. Org. Chem.* 29, 1926–1930 (1964), disclose 2,4,5-tri(p-chlorophenyl)imidazole. There is no disclosure in either reference regarding any biological activity of this compound.

Cherkofsky, et al., U.S. Pat. No. 4,182,769, issued Jan. 8, 1980, disclose compounds of the formula

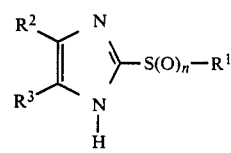

wherein:

n is 0, 1 or 2;

$R^1$ is $C_{1-6}$ alkyl and mono- and polyhalo $C_{1-4}$ alkyl; and $R_2$ and $R_3$ are independently selected from monosubstituted phenyl wherein said substituent is selected from $C_{1-4}$ alkoxy, Cl or F. Cherkofsky, et al. state that such compounds have antiinflammatory activity and analgesic activity as indicated by the adjuvant-induced arthritis assay in rats, which, as stated above, is of no known utility in detecting compounds which are inhibitors of IL-1 production by macrophages and/or monocytes.

Ferrini et al., U.S. Pat. No. 4,461,770, issued July 24, 1984, disclose compounds of the formula

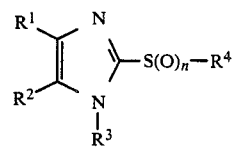

wherein at least one of the radicals $R_1$ and $R_2$ is a substituted or unsubstituted heteroaryl group and the other is a substituted or unsubstituted aryl group; $R_3$ is H or lower alkyl, n is 0, 1 or 2, and $R_4$ is substituted or unsubstituted aliphatic hydrocarbon radical, and pharmaceutically usable salts thereof. Ferrini et al. also disclose that such compounds have anti-inflammatory, antinociceptive and/or anti-thrombotic activity as well as an inhibitory action on prostaglandin synthesis based on their effects in the Kaolin paw oedema test, the carrageenan paw edema test, the phenyl-p-benzoquinone induced writhing assay in mice; the arachidonate induced emboly assay in rabbit lung and the in vitro inhibition of prostaglandin synthesis from arachidonic acid assay. As stated above, none of such assay systems have any known utility for detecting or suggesting compounds which are inhibitors of IL-1 production by macrophages and/or monocytes.

Cherkofsky et al., U.S. Pat. No. 4,159,338, issued June 26, 1979, disclose compounds of the formula

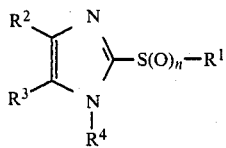

wherein:

n is 0, 1 or 2;

$R_1$ is polyfluoro $C_{1-2}$ alkyl;

$R_2$ and $R_3$ are independently selected from 2-thienyl, 3-thienyl, 3-pyridyl, 2-furyl or monsubstituted phenyl wherein said substituent is selected from $C_{1-4}$ alkoxy, Cl or F, and $R_4$ is H, and pharmaceutically acceptable acid addition salts thereof.

Cherkofsky, et al. also disclose that such compounds have antiinflammatory, antiarthritic and/or analgesic activity based on their activity in the established adjuvant induced arthritis assay in rats and in the phenylquinone writhing test in mice. As stated above, none of such assays are of any known utility in detecting or suggesting compounds which are inhibitors of IL-1 production by macrophages and/or monocytes.

Bender, et al., U.S. Pat. No. 4,175,127, issued Nov. 20, 1979, disclose compounds of the formula

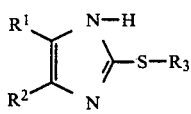

wherein $R_3$ is H, $C_{1-6}$ alkyl or mono- or polyhalo $C_{1-4}$ alkyl; and $R^1$ and $R^2$ are the same or different, but one of which always being pyridyl, are pyridyl or monosubstituted phenyl wherein said substituent is selected from lower alkoxy, chloro, fluoro or bromo. Bender, et al. also disclose that when $R_3$ is H, such compounds are useful only as intermediates, and when $R_3$ is other than H, such compounds have potent antiarthritic activity based on their activity in the adjuvant-induced polyarthritis assay in rats which, as stated above, is of no known utility for detecting or suggesting compounds which are inhibitors of IL-1 production by macrophages and/or monocytes.

Fitzi, et al., U.S. Pat. No. 3,940,486, issued Feb. 24, 1976, and Fitzi et al. U.S. Pat. No. 3,929,807, issued Dec. 30, 1975, disclose compounds of the formula

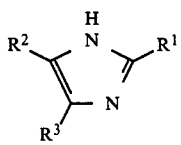

wherein:

$R_1$ is halo-substituted phenyl; and one of the groups of $R_2$ and $R_3$ represents phenyl which is optionally substituted by halo or lower alkoxy and the other is a 6-membered heteroaromatic ring, and salts of such compounds.

Fitzi, et al. also disclose that such compounds have antiinflammatory, antinociceptive and antipyretic action based on their activity in the Bolus alba oedema test in rats; the phenyl-p-benzoquinone-induced writhing assay in mice, and yeast-induced fever assay in rats. As stated above, such assays have no known utility in detecting or suggesting compounds which are inhibitors of IL-1 production by macrophages and/or monocytes.

Lantos, et al., J. Med. Chem., 27(1), 72–75 (1984), disclose 4-(4-methoxyphenyl)-5-(4-pyridyl)-2-thione-imidazole and 4-(4-fluorophenyl)-5-(4-pyridyl)-2-thione-imidazole as intermediates. There is no disclosure in Lantos, et al. regarding any biological activity of such compounds.

Cherkofsky, et al., U.S. Pat. No. 4,199,592, issued Apr. 12, 1980, discloses compounds of the formula

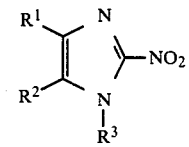

wherein $R_3$ is H; and $R_1$ and $R_2$ are independently selected from pyridyl, thienyl or monosubstituted phenyl wherein said substituent is selected from chloro, fluoro or $C_{1-4}$ alkoxy.

Cherkofsky, et al. also disclose that such compounds have antiinflammatory, antiarthritic and/or analgesic activity based on their activity in the established adjuvant-induced arthritis assay in rats and the phenylquinone induced writhing assay in mice. As stated above, none of such assays either disclose or suggest compounds which are inhibitors of IL-1 production by macrophages and/or monocytes.

SUMMARY OF THE INVENTION

This invention relates to a method of inhibiting the production of Interleukin-1 (IL-1) by monocytes and/or macrophages in a human in need thereof which comprises administering to such human an effective, IL-1 production inhibiting amount of a compound of the formula

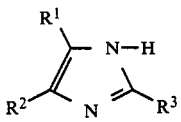

Formula (I)

wherein:

one of $R^1$ and $R^2$ is 4-pyridyl and the other is selected from monohalosubstituted phenyl; and $R^3$ is SH or $SCF_2CF_2H$;

or a pharmaceutically acceptable salt thereof.

DETAILED DESCRIPTION OF THE INVENTION

The preparation of all compounds of Formula (I) and pharmaceutically acceptable salts thereof is disclosed in Bender et al., U.S. patent application Ser. No. 856,927, filed Apr. 28, 1986, the disclosure of which is hereby incorporated by reference.

By the term "inhibiting the production of IL-1" is meant the down regulation of excessive in vivo IL-1 levels in a human to normal levels.

By the term "production of IL-1 by monocytes and/or macrophages" is meant the in vivo release of IL-1 by such cells.

Interleukin-1 (IL-1) has been recently demonstrated to mediate a variety of biological activities thought to be important in immunoregulation and other physiological conditions such as inflammation [See, e.g., Dinarello et al., *Rev. Infect. Disease*, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels. However, much remains to be learned about the synthesis, processing and secretion of IL-1. For example, there is recent evidence suggesting that there are two separate human interleukin-1 genes, and that the products of these two genes differ in their isoelectric points. It is also clear that the published data on the cloning of the cDNA of the IL-1 gene(s) suggest that IL-1 is synthesized as a 31 Kilodalton(Kd) precursor, which is subsequently processed to yield a smaller mature protein of about 17 Kd, the activity of which is detectable in culture supernatants. One interesting feature of the precursor protein is that it lacks a classical signal peptide sequence, suggesting that the molecule is probably not secreted in a classical manner. Ther is very little information available as to how the 31 Kd precursor is processed and secreted.

The discovery of a compound which specifically inhibits IL-1 production will not only contribute to the understanding of how this molecule is synthesized, processed and secreted, but will also provide a therapeutic approach for diseases in which excessive or unregulated IL-1 production is implicated.

It has now been discovered that the compounds of Formula (I) and pharmaceutically acceptable salts thereof are useful for inhibiting the production of IL-1 by mmonocytes and/or macrophages in a human in need of such inhibition.

There are several disease states in which excessive or unregulated IL-1 production by monocytes and/or macrophages is implicated in exacerbating and/or causing the diseases. These include rheumatoid arthritis [See, e.g., Fontanta et al., *Arthritis Rheum.*, 22, 49–53 (1982)]; osteoarthritis [See, e.g., Wood et al., *Arthritis Rheum.*, 26, 975 (1983)]; toxic shock syndrome [See, e.g., Ikejima and Dinarello, *J. Leukocyte Biology*, 37, 714 (1985)]; other acute or chronic inflammatory disease states such as the inflammatory reaction induced by endotoxin [See, e.g., Habicht and Beck, *J. Leukocte Biology*, 37, 709 (1985)]; and other chronic inflammatory disease states such as tuberculosis. [See, e.g., Chesque et al., *J. Leukocyte Biology*, 37, 690 (1985)]. Benjamin et al., "Annula Reports In Medicinal Chemistry-20", Chapter 18, pages 173–183 (1985), Academic Press, Inc., disclose that excessive IL-1 production is implicated in Psoriatic arthritis, Reiter's syndrome, Rheumatoid arthritis, Osteoarthritis, Gout, Traumatic arthritis, Rubella arthritis and Acute synovitis. Dinarello, *J. Clinical ImmunoloqY*, 5(5), 287–297 (1985) reviews the biological activities which have been attributed to IL-1 and such activities are summarized in Table A.

Table A

Biological Activities Attributed to IL-1

Fever (in rabbits, mice and rats)
Hypoferremia
Hypozincemia
Hypercupremia
Increased
   Blood neutrophils
   Hepatic acute-phase proteins
   Bone resorption
   Cartilage breakdown
   Muscle proteolysis
   Slow-wave sleep
   Endothelial procoagulant
   Chondrocyte proteases
   Synovial collagenase
   Endothelial neutrophil adherence
   Neutrophil degranulation
   Neutrophil superoxide
   Interferon production
Proliferation of
   Fibroblasts
   Glial cells
   Mesangial cells
   Synovial fibroblasts
   EBV B-cell lines
Chemotaxis of
   Monocytes
   Neutrophils
   Lymphocytes
Stimulation of $PGE_2$ in
   Hypothalamus
   Cortex
   Skeletal muscle
   Dermal fibroblast
   Chondrocyte
   Macrophage/monocyte
   Endothelium ($PGI_2$)
Decreased
   Hepatic albumin synthesis
   Appetite
   Brain binding of opioids
Augmentation of
   T-cell responses
   B-cell responses
   NK activity
   IL-2 production
   Lymphokine production An effective, IL-1 production inhibiting amount of a compound of Formula (I) or a pharmaceutically acceptable salt thereof is useful in treating, prophylactically or therapeutically, any disease state in a human which is exacerbated or caused by the overproduction of IL-1 by such human's macrophages and/or monocytes.

This invention relates to a method of inhibiting the production of IL-1 by monocytes and/or macrophages in a human in need thereof which comprises administering an effective, IL-1 production inhibiting amount of a compound of Formula (I) or a pharmaceutically acceptable salt thereof to such human. A compound of Formula (I) or a pharmaceutically acceptable salt thereof can be administered to such human in conventional dosage form prepared by combining a compound of Formula (I), or a pharmaceutically acceptable salt thereof can be administered to such human in a conventional dosage form prepared by combining a compound of Formula (I) with a conventional pharmaceutically acceptable carrier or diluent according to known techniques, such as those described in Bender et al., U.S. Ser. No. 856,927 filed Apr. 28, 1986. It will be recognized by one of skill in the art that the form and character of the pharmaceutically acceptable carrier or diluent is dictated by the amount of active ingredient with which it is to be combined, the route of administration and other well-known variables. A compound of Formula (I) or a pharmaceutically acceptable salt thereof is administered to a human in need of inhibition of IL-1 production by its monocytes and/or macrophages in an amount sufficient to inhibit such IL-1 production down to normal levels. The route of administration may be oral, parenteral or topical. The term parenteral as used herein includes intravenous, intramuscular, subcutaneous intranasal, intrarectal, intravaginal or intraperitoneal administration. The intravenous and intramuscular forms of parenteral administration are generally preferred. The daily parenteral dosage regimen will preferably be from about 2 to 100 mg per kilogram (kg) of total body weight, preferably from about 3 to about 30 mg/kg. The daily oral dosage regimen will preferably be from about 3 to 100 mg/kg of total body weight, preferably from about 3 to 30 mg/kg. The daily topical dosage regimen will preferably be from about 2 to 10 mg per site of administration. It will be recognized by one of skill in the art that the optimal quantity and spacing of individual dosages of a of Formula (I) or a pharmaceutically acceptable compound salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable acid addition salt thereof given per day for a defined number of days, can be ascertained by those skilled in the art using conventional course of treatment determination tests.

EXAMPLES

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLE 1

Inhibitory Effect of a Compound of Formula (I) on in vitro IL-Production by Human Monocytes The inhibitory effect of several compounds of Formula (I) on in vitro IL-1 production by human monocytes was determined by the following method.

Bacterial lipopolysaccharide (LPS) was used to induce IL-1 production by human peripheral blood monocytes. IL-1 activity was measured by its ability to stimulate a Interleukin 2 (IL-2) producing cell line (EL-4) to secrete IL-2, in concert with A23187 ionophore, according to the method of Simon et al., *J. Immunol. Methods*, 84, 85-94. (1985). Human peripheral blood monocytes [isolated and purified from either fresh blood preparations from volunteer donors, or from blood bank buffy coats, according to the method of Colotta et al., *J. Immunol.*, 132, 936 (1984)]were isolated and purified from either fresh blood preparations from volunteer donors, or from Blood Bank buffy coats, according to the procedure of Colotta et al., *J. Immunol.*, 132, 936 (1984). $1 \times 10^6$ human peripheral blood monocytes at a concentration of 2 million/ml per well, were plated in 24-well plates and allowed to adhere for 1 hour (hr) at 37° C. The compounds of Formula (I) were added to a final concentration of $10^{-5}$M to $10^{-8}$M. The monocytes were stimulated to produce IL-1 with 10 ng/ml LPS after a 1 hr pretreatment of the cells with the respective compounds. The cultures were incubated at 37C for an additional 24 hours, and then culture supernatants were removed and clarified of cells and all debris, and were immediately assayed for IL-1 biological activity by radioimmunoassay.

The results indicated that human peripheral blood monocytes are exquisitely sensitive to bacterial endotoxin (LPS). Nanogram or even picogram quantities of LPS stimulated high levels of IL-1 production.

In this assay, ibuprofen, a highly active inhibitor of prostaglandin synthesis, had virtually no effect on IL-1 production at concentrations of $10^{-5}$M, $10^{-6}$M and $10^{-7}$M and the 5-lipoxygenase inhibitors phenidone and nordihydroquaiaretic acid were only marginally active in the inhibition of IL-1 production at a concentration of $10^{-6}$M.

Table 1 summarizes the results obtained with Formula (I) compounds and shows that compounds of Formula (I) inhibit IL-1 production.

TABLE 1

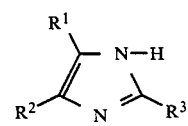

Formula (I)

| Compound No. | R₁ | R₂ | R₃ | % Inhibition @ $10^{-6}$ M |
|---|---|---|---|---|
| 1 | 4-fluorophenyl | 4-pyridyl | SH | 59 |
| 2 | 4-fluorophenyl | 4-pyridyl | SCF₂CF₂H | 78 |

Based on the widely held belief of the role of unmodulated (i.e., excessive) in vivo IL-1 production in causing or aggravating inflammatory responses and other disease states (see, e.g., Fontana et al., supra; Wood et al., supra; Ikejima and Dinarello, supra; Habicht and Beck, supra; Chesque et al., supra; Banjamin et al., supra and Dinarello, supra), and based on the fact that compounds of Formula (I) inhibit in vitro IL-1 production by human macrophages and/or monocytes (see Table I), it is expected that all compounds of Formula (I) inhibit the in vivo IL-1 production by monocytes and/or macrophages in a human in need thereof when used according to the method of the subject invention.

What is claimed is:

1. A method of inhibiting the production of interleukin-1 by monocytes and/or macrophages in a human in need thereof which comprises administering to such human an effective, interleukin-1 production inhibiting amount of a compound of the formula $$\begin{array}{c} R^1 \\ \diagdown \\ \diagup \!\!\!- N\!\!-\!\!H \\ R^2 \diagup \!\!\! \diagdown_N \diagdown R^3 \end{array}$$

wherein:
One of $R^1$ and $R^2$ is 4-pyridyl and the other is selected from monohalosubstituted phenyl; and
$R^3$ is SH or $SCF_2CF_2H$;
or a pharmaceutically acceptable salt thereof.

2. The method of claim 1 wherein the route of administration is parenteral.

3. The method of claim 2 wherein the route of administration is intravenous or intramuscular.

4. The method of claim 2 wherein the compound is administered on a daily dosage regimen of from about 2 to about 100 mg per kg of total body weight.

5. The method of claim 4 wherein the daily dosage regimen is from about 3 to about 30 mg/kg of total body weight.

6. The method of claim 1 wherein the route of administration is oral.

7. The method of claim 6 wherein the compound is administered on a daily dosage regimen of from about 3 to about 100 mg/kg of total body weight.

8. The method of claim 7 wherein the daily dosage regimen is from about 3 to about 30 mg/kg.

9. The method of claim 1 wherein the route of administration is topical.

10. The method of claim 9 wherein the daily topical dosage regimen is from about 2 to about 10 mg per site of administration.

11. The method of claim 1 wherein $R^1$ is 4-fluorophenyl, $R^2$ is 4-pyridyl and $R^3$ is SH.

12. The method of claim 1 wherein $R^1$ is -fluorophenyl, $R^3$ is 4-pyridyl and $R^3$ is $SCF_2CF_2H$.

* * * * *

UNITED STATES PATENT AND TRADEMARK OFFICE
CERTIFICATE OF CORRECTION

PATENT NO. : 4,780,470

DATED : October 25, 1988

INVENTOR(S) : Bender et al

It is certified that error appears in the above-identified patent and that said Letters Patent is hereby corrected as shown below:

Claim 12, column 12, line 13, "-fluoro-" should read -- 4-fluoro --.

Signed and Sealed this

Fourteenth Day of March, 1989

Attest:

DONALD J. QUIGG

*Attesting Officer*   *Commissioner of Patents and Trademarks*